(12) United States Patent
Gupta et al.

(10) Patent No.: US 9,422,354 B2
(45) Date of Patent: Aug. 23, 2016

(54) PROCESS FOR PURIFICATION OF RECOMBINANT GRANULOCYTE COLONY STIMULATING FACTOR (RHU GCSF)

(71) Applicant: INDIAN INSTITUTE OF TECHNOLOGY DELHI, New Delhi (IN)

(72) Inventors: Darpan Gupta, New Delhi (IN); Rahul Bhambure, New Delhi (IN); Rohit Sharma, New Delhi (IN); Anurag Singh Rathore, New Delhi (IN)

(73) Assignee: Indian Institute of Technology Delhi, New Delhi (IN)

( * ) Notice: Subject to any disclaimer, the term of this patent is extended or adjusted under 35 U.S.C. 154(b) by 139 days.

(21) Appl. No.: 13/921,891

(22) Filed: Jun. 19, 2013

(65) Prior Publication Data
US 2014/0030213 A1   Jan. 30, 2014

(51) Int. Cl.
| | |
|---|---|
| *C07K 1/36* | (2006.01) |
| *B01D 15/26* | (2006.01) |
| *B01D 15/38* | (2006.01) |
| *C07K 14/535* | (2006.01) |

(52) U.S. Cl.
CPC .................................... *C07K 14/535* (2013.01)

(58) Field of Classification Search
None
See application file for complete search history.

(56) References Cited

FOREIGN PATENT DOCUMENTS

| | | | | |
|---|---|---|---|---|
| DE | WO 2011121031 A1 * | 10/2011 | ......... | B01D 15/3847 |
| IN | WO 2010146599 A1 * | 12/2010 | ........... | C07K 14/535 |
| WO | 2010146599 | 12/2010 | | |
| WO | WO 2010146599 A1 * | 12/2010 | | |
| WO | WO 2011121031 A1 * | 10/2011 | | |

OTHER PUBLICATIONS

Nomoura et al. Purifcation and characterization of human granulocyte colony stimulating factor. EMBO. 5(5): 871-976, 1986.*

Albertsson, "Partition of Cell Particles and Macromolecules in Polymer Two-Phase Systems," Advances in Protein Chemistry, 1970, 24, 309-341.
Andrews, et al., "Partitioning and purification of monoclonal antibodies in aqueous two-phase systems," Bioseparation 6: 303-313, 1996.
Andrews, et al., Protein partitioning equilibrium between the aqueous poly(ethylene glycol) and salt phases and the solid protein phase in poly(ethylene glycol)-salt two-phase systems. Journal of Chromatography B, 685 (1996) 15-20.
Azevedo, et al., "Affinity-enhanced purification of human antibodies by aqueous two-phase extraction," Separation and Purification Technology, 65 (2009) 31-39.
Azevedo, et al., "Downstream processing of human antibodies integrating an extraction capture step and cation exchange chromatography," Journal of Chromatography B, 877 (2009) 50-58.
Azevedo, et al., "Integrated process for the purification of antibodies combining aqueous two-phase extraction, hydrophobic interaction chromatography and size-exclusion chromatography," Journal of Chromatography A, 1213 (2008) 154-161.
Azevedo, et al., "Optimisation of aqueous two-phase extraction of human antibodies," Journal of Biotechnology 132 (2007) 209-217.
Azevedo, et al., "Partitioning of human antibodies in polyethylene glycol—sodium citrate aqueous two-phase systems," Separation and Purification Technology, 65 (2009) 14-21.
Ferreira, et al., "Purification of human immunoglobulin G by thermoseparating aqueous two-phase systems," Journal of Chromatography A, 1195 (2008) 94-100.
Rosa, et al., "Application of central composite design to the optimisation of aqueous two-phase extraction of human antibodies," Journal of Chromatography A, 1141 (2007) 50-60.
Rosa, et al., "Aqueous two-phase systems: A viable platform in the manufacturing of biopharmaceuticals," Journal of Chromatography A, 1217 (2010) 2296-2305.
Rosa, et al., "Downstream processing of antibodies: Single-stage versus multi-stage aqueous two-phase extraction," Journal of Chromatography A, 1216 (2009) 8741-8749.

* cited by examiner

*Primary Examiner* — Vanessa L Ford
*Assistant Examiner* — Sandra Dillahunt
(74) *Attorney, Agent, or Firm* — K&L Gates LLP

(57) ABSTRACT

The present invention relates to methods for purification of recombinant human granulocyte colony stimulating factor (rHu GCSF). The present invention particularly relates to methods for purification of rHu GCSF involving techniques such as aqueous two phase extraction and multimodal chromatographic purification to obtain highly purified rHu GCSF. The present invention also provides a pharmaceutical composition comprising the rHu GCSF, purified using the methods described herein.

10 Claims, 6 Drawing Sheets

PROCESS FOR PURIFICATION OF RECOMBINANT GRANULOCYTE COLONY STIMULATING FACTOR (RHU GCSF)

CROSS REFERENCE TO RELATED APPLICATION

This patent application claims priority under 35 U.S.C. §119 to Indian Patent Application No. 1880/DEL/2012, filed on Jun. 19, 2012, which is incorporated herein by reference in its entirety.

FIELD OF THE INVENTION

The present invention relates to process for purification of recombinant human granulocyte colony stimulating factor (rHu GCSF) from inclusion bodies expressed in microbial cells.

BACKGROUND OF THE INVENTION

Granulocyte colony stimulating factor (GCSF) is a cytokine produced by macrophages, endothelial cells, monocytes, and fibroblasts. Human GCSF consists of 174 amino acids with an approximate molecular weight of 19.60 kDa. GCSF plays a critical role in the modulation of neutrophil biology. GCSF is required for maintaining an adequate basal neutrophil count, as well as for the generation of an appropriate neutrophilia in response to infectious stimuli. GCSF stimulates the survival, proliferation, differentiation, and function of neutrophil precursors and mature neutrophils. It regulates them using janus kinase (JAK)/signal transducer and activator of transcription (STAT) and ras/mitogen-activated protein kinase (MAPK) and phosphatidylinositol 3-kinase (PI3K)/protein kinase B (AKT) signal transduction pathways.

GCSF increases the neutrophil cell division and decreases marrow transit time, leading to an increase in the total amount of neutrophils. Secondary effects of rHu GCSF on neutrophils include attraction and localization to sites of infection, increase in phagocytosis and a decrease in apoptosis. rHu GCSF was approved by FDA for use in chemotherapy induced neutropenia m 1991 (Global Regulatory Affairs, Sanofi US). rHu GCSF is a 175 amino acid non glycosylated protein expressed in *E. coli* with molecular weight of 18.8 kDa. rHu G-CSF contains an additional N-terminal methionine, which is essential for its expression in *E. coli* cells.

The expression of recombinant proteins is mainly achieved by using prokaryotic or eukaryotic expression systems. Prokaryotic expression systems offer several advantages including, cost, culture conditions, rapid cell growth, yield and relatively short expression time over eukaryotic expression systems. However the key drawback associated with the prokaryotic expression system is the absence of glycosylation. rHu G-CSF produced using *E. coli* cells forms inclusion bodies in the form of insoluble protein aggregates.

The development of cost effective and efficient downstream processes is an essential part of the biopharmaceutical manufacturing processes. Process robustness, scalability, reproducibility, and capability of selective removal of product and process related impurities are essential requirements of an industrial biopharmaceutical manufacturing process. Breakthrough discoveries in molecular biology and upstream processes in recent years are responsible for higher recombinant protein titre which has shifted the overall economics of manufacturing processes towards downstream processing. Although this bottleneck can be overcome by scaling up the process, there still exists a physical limit of existing facilities throughput and scalability. With biotechnology companies operating under ever-increasing pressure towards lowering the cost of manufacturing processes, integration of cost effective alternative purification strategy is the need of the hour. This problem clearly defines the need for efficient purification strategies for manufacturing of recombinant proteins. In view of this bioprocess technologists are investigating the role of alternative purification strategies which are capable of providing economically efficient large scale processes. Few alternatives among these are, use of precipitation or selective extraction techniques for the isolation of the product of the interest. Aqueous two phase system (ATPS) is an attractive alternative which offers a solution to the above mentioned problems, by increasing the overall throughput and minimizing the cost of manufacturing the product.

Aqueous two phase systems forms as a result of the incompatibility between two aqueous phases of various polymers or the salt solutions. Albertson in 1955 demonstrated use of polyethylene glycol and phosphate based aqueous two phase system as separation tool for downstream processing of various biological molecules (Albertsson, P. Å. Advances in Protein Chemistry, 1970, 24, 309-341). Till date aqueous two phase system based separation processes has been applied to many biological systems which mainly include purification of proteins, nucleic acids, plant or animal cells, microorganisms etc. Selective isolation of the target protein in one of the phases of aqueous two phase system forms the basis of the purification in ATPS. Process parameters which affect this selectivity in partioning includes type of the polymers, type of the salt, concentration of polymer as well as salt, pH of the system, ionic strength of the system etc. Certain properties of biological molecules affect the selectivity, such as charge, hydrophobicity, molecular weight, conformation etc.

In the recent years there is a paradigm shift in the application of the aqueous two phase system from crude purification technique for cell or microorganism separation to polishing step technique for downstream processing of biologicals. Rosa et al have enlisted the application of aqueous two phase systems for purification of various biopharmaceutical proteins (Rosa et al., Journal of Chromatography, 2010, 1217, 2296-2305; Rosa et al., *Journal of Chromatography A*, 2007, 1141, 50-60; Rosa et al., *Journal of Chromatography A*, 2009, 1216, 8741-8749; Rosa et al., *Journal of Chromatography A*, 2010, 1217, 2296-2305). However in comparison to the existing techniques such as chromatography the recovery and purity values which are obtained using ATPS is still a fact of the concern. For various biopharmaceuticals using aqueous two phase systems the recovery values range from 50-95% with the purity levels ranging from 76-95% (Andrews et al., *Journal of Chromatography B: Biomedical Sciences and Applications*, 1996, 685, 5-20; Andrews et al., *Bioseparation*, 1996, 6, 303-313; Azevedo et al., *Separation and Purification Technology*, 2009, 65, 14-21; Azevedo et al., *Journal of Chromatography A*, 2008, 1213, 154-161; Azevedo et al., *Journal of Biotechnology*, 2007, 132, 209-217; Azevedo et al., *Journal of Chromatography B: Analytical Technologies in the Biomedical and Life Sciences*, 2009, 877, 50-58; Azevedo et al., *Separation and Purification Technology*, 2009, 65, 31-39; Ferreira et al., *Journal of Chromatography A*, 2008, 1195, 94-100).

WO 2010146599 describes the application of aqueous two phase system for the purification of rHu GCSF. The recovery of rHu GCSF from the process employed is 40% to 50%.

Further, isolation of various product related impurities in biopharmaceutical proteins is achieved using various chromatographic techniques. Different chromatographic techniques are based on the differences in physicochemical interaction of the components with the resin matrix. Various commonly used include affinity, ion exchange, and hydrophobic interaction-chromatography. Ion-exchange chromatography (IEC) forms the backbone of most biopharmaceutical drug purification processes as it offers high selectivity for isolation of various process and product related impurities.

In the current era of "biosimilars", additional challenges have been imposed on chromatography process development for matching the product purity profile to the innovator's molecule. Although ion exchange chromatography offers a solution for selective isolation of various product related impurities, critical drawback associated with conventional ion exchange matrix involves intolerance to the high ionic strength protein solutions, need of the buffer exchange step for lowering ionic strength of the process intermediate samples which in turn increases the cost of the manufacturing.

SUMMARY OF THE INVENTION

An aspect of the present invention relates to a method of purifying recombinant human granulocyte colony stimulating factor (rHu GCSF) from a recombinant host cell, wherein the method comprises: obtaining rHu GCSF from a recombinant host cell in the form of inclusion bodies; solubilizing inclusion bodies using a solubilization buffer to obtain solubilized rHu GCSF; refolding the solubilized rHu GCSF using a refolding buffer to obtain refolded rHu GCSF; concentrating the refolded rHu GCSF by ultra-filtration to obtain concentrated rHu GCSF; subjecting the concentrated rHu GCSF to aqueous two phase extraction to remove host cell proteins and host cell DNA and to obtain rHu GCSF partitioned into polymeric phase and in the form of precipitate between the two aqueous phases; resolubilizing the rHU GCSF using a resolubilization buffer to obtain rHU GCSF solution; and subjecting the rHU GCSF solution to chromatography purification to remove product related impurities and obtain purified rHU GCSF. The different chromatography purification methods which can be used for purification of rHu GCSF are ion exchange chromatography, hydrophobic chromatography, and multimodal chromatography.

Another aspect of the present invention relates to a method for purifying recombinant human granulocyte colony stimulating factor (rHu GCSF) from a recombinant host cell, wherein the method comprises: obtaining rHu GCSF from a recombinant host cell in the form of inclusion bodies; solubilizing inclusion bodies using a solubilization buffer to obtain solubilized rHu GCSF; refolding the solubilized rHu GCSF using a refolding buffer to obtain refolded rHu GCSF; concentrating the refolded rHu GCSF by ultra-filtration to obtain concentrated rHu GCSF; subjecting the concentrated rHu GCSF to multimodal chromatography to remove product related impurities, host cell proteins, and host cell nucleic acids and obtain purified rHu GCSF.

This summary is provided to introduce concepts related to methods of purifying recombinant human granulocyte colony stimulating factor (rHu GCSF). This summary is not intended to identify essential features of the claimed subject matter nor is it intended for use in determining or limiting the scope of the claimed subject matter.

BRIEF DESCRIPTION OF ACCOMPANYING DRAWINGS

The following drawings form part of the present specification and are included to further illustrate aspects of the present invention. The invention may be better understood by reference to the drawings combination with the detailed description of the specific embodiments presented herein.

Figure 3:
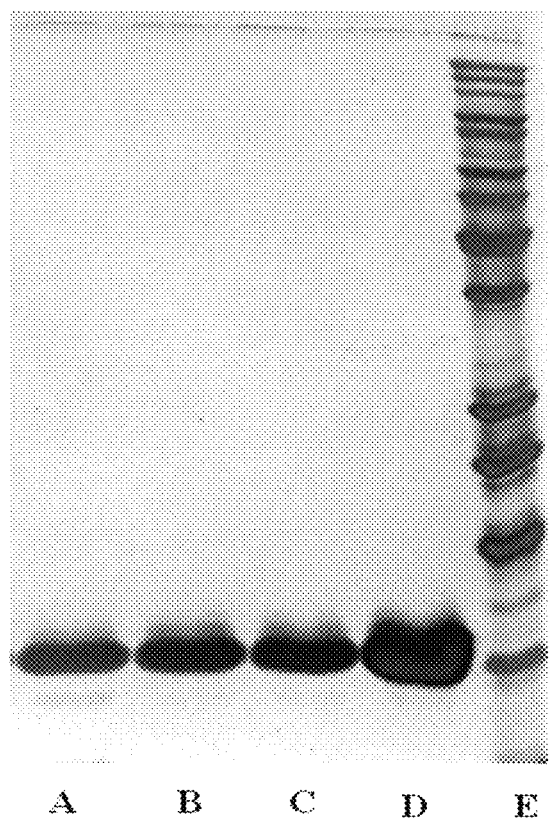

FIG. 3 shows the SDS PAGE profile for characterization of low and high molecular weight impurities associated with rHu GCSF (Lane A: GCSF Standard (0.2 mg/ml) with low molecular weight impurities; Lane B: GCSF purified using the multimodal chromatography step of present invention; Lane C: GCSF purified using the multimodal chromatography step of present invention replicate run; Lane D: GCSF standard (0.2 mg/ml); Lane E: Molecular weight marker).

Figure 4:
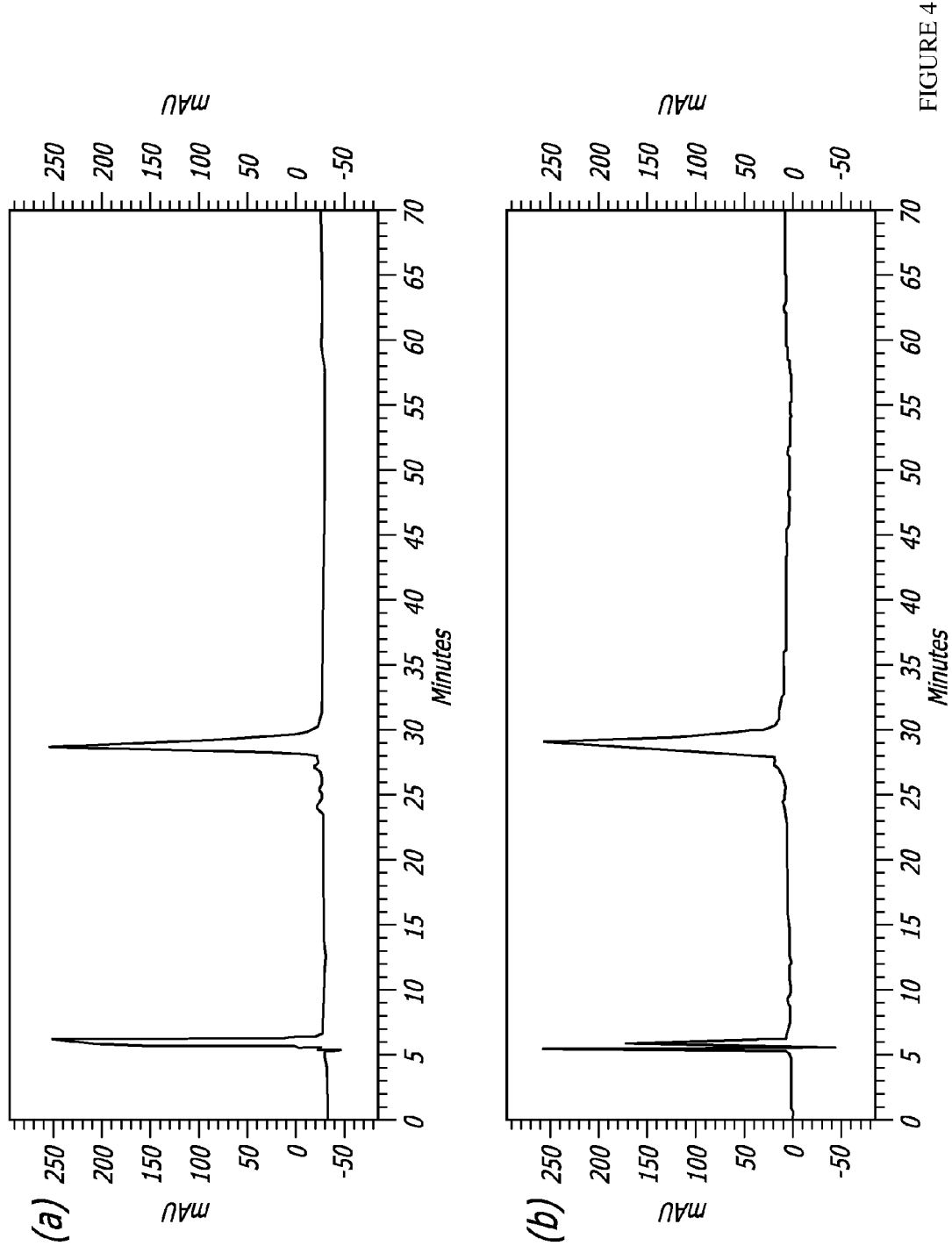

FIG. 4 shows the chromatogram for reverse phase high performance liquid chromatography (RP-HPLC) for purity analysis of rHu GCSF purified using the process; A. Standard rHu GCSF; B. rHu GCSF purified using the process described in the present invention.

Figure 5:
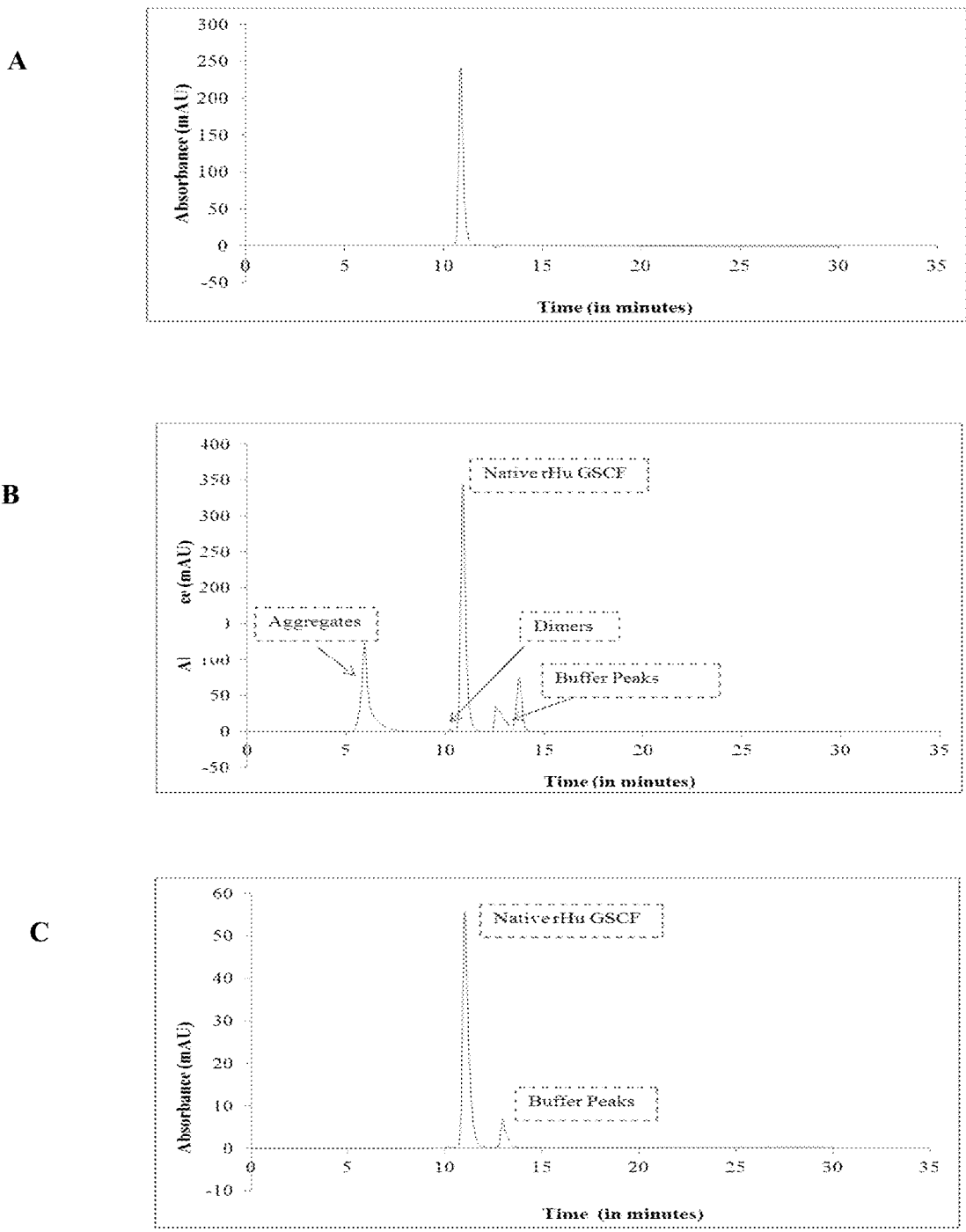

FIG. 5 shows the size exclusion chromatogram for rHu GCSF produced using the process described in the present invention; A. Standard rHu GCSF; B. Pretreated refold output for aqueous two phase extraction; C. rHu GCSF purified using the multimodal chromatography purification.

Figure 6:
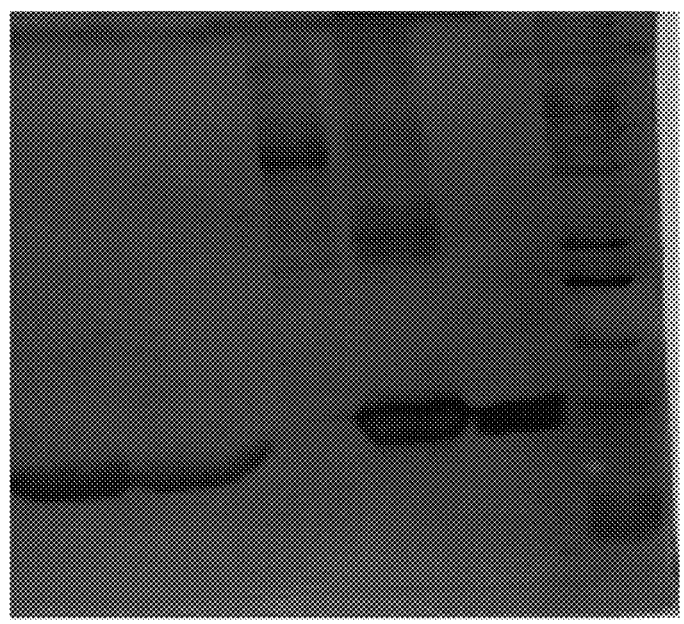

FIG. 6 shows the SDS PAGE purity profile for rHu G-CSF purified using the process described in the present invention (Lane 1: multimodal chromatography output; Lane 2: two phase extraction output; Lane 3: standard host cell proteins; Lane 4: refolded protein after pH adjustment; Lane 5: standard rHu G-CSF; and Lane 6: molecular weight marker).

DETAILED DESCRIPTION OF THE INVENTION

Those skilled in the art will be aware that the invention described herein is subject to variations and modifications other than those specifically described. It is to be understood that the invention described herein includes all such variations and modifications. The invention also includes all such steps, features, compositions, and compounds referred to or indicated in this specification, individually or collectively, and any and all combinations of any two or more of said steps or features.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a", "an", and "the" are used to refer to one or to more than one (i.e., to at least one) of the grammatical object of the article.

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "target protein" or "target molecule" refers to the rHu GCSF; which is the aim of the method to purify of.

The term "inclusion bodies" refers to intracellular aggregates of "target protein". Inclusion bodies of the target protein contain combination of misfolded and partially folded protein.

The term "protein refolding" refers to process of converting the misfolded form of the "target protein" to the correctly folded form.

The term "reducing agent" refers to the chemical entity which causes reduction of the disulphide linkages of the protein and maintains both intra and inter molecular disulfide bonds chemically disrupted.

The term "chaotropic agent" refers to the chemical entity which is capable of altering the protein conformation making it more water soluble. Chaotropic agent increases entropy of the system by interfering with intramolecular interactions mediated by non covalent forces. Examples of such chaotropic agent include ethanol, butanol, urea, thiourea, magnesium chloride, lithium perchlorate etc.

The term "host cell protein" refers to all the proteins which are expressed by the host cell apart from the target protein during the course of fermentation or cell culture process.

The term "top phase" refers to the less density phase which collects above the bottom phase during the formation of aqueous two phase system.

The term "bottom phase" refers to the more density phase which collects at the bottom during the formation of aqueous two phase system.

The term "multimodal chromatography" refers to chromatography technique in which the ligand interacts with the components protein through multiple types of interactions which involves ionic interaction, hydrophobic interaction or hydrogen boding etc. The type of the interaction with particular type of the protein is mainly affected by the operating conditions.

The present invention is not to be limited in scope by the specific embodiments described herein, which are intended for the purposes of exemplification only. Functionally-equivalent products, compositions, and methods are clearly within the scope of the invention, as described herein.

The present invention provides a process for purification of rHu GCSF, the process comprising solubilizing rHu GCSF inclusion bodies, refolding the solubilized rHu GCSF, ultra-filtering and adjusting the pH of rHu GCSF to obtain concentrated rHu GCSF, subjecting concentrated rHu GCSF to aqueous two phase extraction and obtaining rHu GCSF as a precipitate in between two aqueous phases as well as partitioned into polymer, resolubilizing the precipitate by using resolubilization buffer and subjecting the resolubilized rHu GCSF to multimodal chromatography purification.

The process for purification of rHu GCSF as described in the present invention provides for removal of process related impurities, namely host cell proteins and nucleic acids (DNA) as well as product related impurities from human GCSF produced recombinantly.

The rHu GCSF inclusion bodies were solubilized using suitable solubilization buffer containing a combination of chaotropic reagent and reducing agent. The solubilization buffer includes but not limited to phosphate, histidine, glycine, HEPES, MOPS, carbonate-bicarbonate buffer, and Tris chloride buffer. Chaotropic reagent includes urea and guanidium hydrochloride salts. The pH of solubilization buffer was adjusted to 9-12. Reduction of the solubilized inclusion bodies was achieved using a combination of the reducing agents which includes dithiothreitol, beta mercaptoethanol, and sodium borohydride in the temperature range of 5° C. to 35° C.

The inclusion bodies solubilized previously were refolded using a suitable refolding buffer in the temperature range of 5° C. to 30° C. The refolded product was analyzed by RP-HPLC for measuring the unfolded and refolded forms of the product. Refolding buffer components include but not limited to tris, urea, arginine, EDTA, histidine, sodium phosphate, potassium phosphate, along with a combination of the redox couple reagents such as cysteine/cystine, cystamine/cystamine, and oxidized and reduced glutathione. The time required for refolding varies from 3 hours to 25 hours.

After the refolding of rHu GCSF, protein was concentrated by ultra-filtration. The pH of the concentrated protein sample was then adjusted to pH 3.00 to 5.70. The protein sample was then centrifuged at 8000 rpm (4° C.) and used as an input for aqueous two phase extraction step.

The various process related impurities associated with rHu GCSF were isolated using aqueous two phase extraction process. Aqueous two phase extraction of rHu GCSF involved the integration of two novel steps namely, forward extraction and resulobilization of precipitate. First forward extraction step involved the formation of two phases, involving two miscible aqueous phases and a precipitate of the target protein. The addition of the phase forming components such as polymer and salt to the protein solution leads to the formation of two aqueous phase system. The process related impurities such as E. coli host cell proteins and double stranded DNA partitioned into the salt rich bottom phase. During forward extraction, a combination of salting out and electrostatic interaction leads to the precipitation of the target protein at the interface. A thick layer of precipitate was observed at the interface of top and bottom phase which comprised rHu GCSF. rHu GCSF was also portioned in the top phase. The precipitate formed during forward extraction step may be recovered by microfiltration, centrifugation or draining of the either/both polymer and salt phases. Hence, the precipitate could be recovered separately, or along with one of the polymer or salt phases.

Two phase system is formed by adding appropriate amount of polymer, salt and protein solution, and mixing the solution slowly for several minutes. The mixture is then left to settle. Suitable polymer examples include but not limited to ethylene oxide and propylene oxide (copolymer) (EOPO), and polyethylene glycol of varying molecular weight. A phase forming salt includes but not limited to sodium phosphate (monobasic and dibasic salts), potassium phosphate (monobasic and dibasic salts), sodium sulphate, calcium sulphate, potassium phosphate, ammonium sulphate, ammonium phosphate, manganese sulphate, manganese phosphate, and calcium phosphate.

We performed aqueous two phase extraction covering a range of polymer concentration and salt concentration. The polymer concentration was varied from 7.5% to 15.5% (w/w) to the final solution concentration and salt concentration was varied from 7.5% to 15.5% (w/w) to the final solution concentration. We found that the suitable polymer concentration was in the range of 10.0% to 15.5%, preferably 11.5%, 13.5%, and 15.5%. Further, the suitable salt concentration was found in the range of 8.5% to 12%, preferably 9.5%, and 11.5%. The combination of polymer at a concentration of 11.5% with salt at a concentration of 9.5% gave promising results and led to a recovery of 99.96% of rHu GCSF with host cell protein concentration less than 100 ppm and DNA concentration less than 10 ng. In an embodiment of the present invention, PEG 6000 (as polymer) at a final solution concentration of 11.5% and sodium sulphate (as salt) at a final solution concentration of 9.5% has been shown to provide excellent purification of rHu GCSF with maximum removal of process related impurities. Table 1 lists the various conditions of polymer and salt concentration which were examined for the optimization of polymer and salt concentrations along with the rHu GCSF recovered from the different sets of experiments.

TABLE 1

List of conditions examined for optimization of polymer and salt concentration

| S. No. | Polymer concentration (%) | Salt concentration (%) | GCSF Recovery (%) |
|---|---|---|---|
| 1 | 7.5 | 15.5 | 86.81 |
| 2 | 7.5 | 15.5 | 85.83 |
| 3 | 11.5 | 15.5 | 82.23 |
| 4 | 11.5 | 15.5 | 82.05 |
| 5 | 15.5 | 15.5 | 71.96 |
| 6 | 15.5 | 15.5 | 70.50 |
| 7 | 11.5 | 13.5 | 80.58 |
| 8 | 7.5 | 11.5 | 80.36 |
| 9 | 7.5 | 11.5 | 80.42 |
| 10 | 9.5 | 11.5 | 88.93 |
| 11 | 11.5 | 11.5 | 92.73 |
| 12 | 11.5 | 11.5 | 94.62 |
| 13 | 11.5 | 11.5 | 92.25 |
| 14 | 11.5 | 11.5 | 92.70 |
| 15 | 13.5 | 11.5 | 91.33 |
| 16 | 15.5 | 11.5 | 90.34 |
| 17 | 15.5 | 11.5 | 90.01 |
| 18 | 11.5 | 9.5 | 99.96 |
| 19 | 7.5 | 7.5 | 87.80 |
| 20 | 7.5 | 7.5 | 85.80 |
| 21 | 11.5 | 7.5 | 101.71 |
| 22 | 11.5 | 7.5 | 100.74 |
| 23 | 15.5 | 7.5 | 100.62 |
| 24 | 15.5 | 7.5 | 99.96 |

The patent publication WO 2010146599 discloses the purification of rHu GCSF using aqueous two phase extraction where the recovery of protein is in the range of 40% to 50%. The applicant performed an analysis of the recovery of rHu GCSF after carrying out aqueous two phase extraction. Surprisingly, we found that we got a higher recovery of more than 90% (Table 1) of rHu GCSF after aqueous two phase extraction. The results can be attributed to the fact that the applicant extracted rHu GCSF from the top phase as well as the precipitate layer formed between the two aqueous phases. For further purification the applicant can perform purification using different chromatography purification methods. The chromatography purification can be performed either by ion exchange chromatography, or hydrophobic chromatography, or multimodal chromatography.

The process related impurities were removed to the maximum level with the use of aqueous two phase extraction process. rHu GCSF was further subjected to chromatography purification such as multimodal chromatography to remove the product related impurities. After the precipitate recovery, protein precipitate was solubilized using resolubilization buffer comprised of but not limited to acetate, phosphate, citrate, containing sorbitol, arginine, cysteine, and cysteine. The pH of resulobilization buffer varied from 3.00 to 5.70. The choice of resolubilizing buffer depends on the specific characteristics of the target protein as well as the next purification step being employed in the process. In an embodiment of the present invention, a buffer solution at a pH 4.00 is chosen for purification of rHu GCSF.

The time and method chosen for solubilising depends on the behaviour of the target protein as well as the resolubilizing buffer being used for resolubilizing. The resolubilization of precipitate should be done within twenty hours of initial precipitate formation, for instance 1 hour. The solution may then be centrifuged to obtain a clear supernatant. In one embodiment of the present invention, following the resolublization of the precipitate for 10 minutes by shaking on the rocker shaker, protein solution is centrifuged at 8000 rpm at 4° C. The supernatant is then filtered using microfiltration and used as an input for multimodal chromatography step.

Multistep purification platform used in purification of protein mainly involves combination of ion exchange chromatography along with hydrophobic interaction chromatography for isolation of various product related impurities. In particular, process described in the present invention, the "multimodal" chromatography resin is selected from the following commercially resins but not limited to Ceramic Hydroxyapatite (CHTTM), HEP Hypercel, Capto MMC, PPA Hypercel, Capto Adhere, and MEP Hypercel.

The multimodal chromatography step was processed for the isolation of various product related impurities such as oxidized and reduced form of rHu GCSF. We performed multimodal chromatography with three different resins namely Capto MMC, HEP Hypercel, and PPA Hypercel. The experiments were conducted with different equilibration and elution buffers having varied concentration of buffer, pH and salt.

The experiment to capture the protein using Capto MMC was done by full factorial design to identify the binding conditions for rHu GCSF. Acetate buffer of pH varying from 4.00 to 5.70 containing 0 to 330 mM sodium chloride concentration was used for the equilibration buffer. The effect of these two process variables on the binding behaviour of the protein was investigated. It was observed that both pH and salt concentration significantly affect the interaction of rHu GC SF to the Capto MMC resin. It was observed in all the experiments that approximately 50% rHu GCSF was obtained in the flow through. An increase in salt concentration was helpful in improving the binding of rHu GCSF to the Capto MMC resin matrix at a selected pH. In an embodiment of the present invention, the experiment was conducted using 35 mM acetate (without containing salt) at pH 5.70 as the equilibration buffer. Under these experimental conditions, 52.30% of rHu GCSF was observed in flowthrough. Elution buffer used for this experimental setup was 35 mM acetate at pH 5.70 containing 1M NaCl, wherein no protein was observed in the elution. However, the low recovery of rHu GCSF using Capto MMC led to further experiments using other resins i.e., HEA Hypercel and PPA Hypercel.

Full factorial design was used to identify the binding conditions for rHu GCSF. 35 mM to 70 mM acetate and tris buffer of pH varying from 5 to 7 containing 0 to 300 mM sodium chloride concentration was used for the equilibration of PPA Hypercel and HEA Hypercel. Different combinations of pH, salt and buffer concentrations were examined to reach at the optimum concentrations of equilibration buffer. Both HEA and PPA Hypercel resins were equilibrated with 35 mM acetate at pH 5.70. The elution was performed using a gradient with 100 mM acetate, pH 3.50 for both HEA and PPA Hypercel resins. It was observed that under these conditions, a recovery of 52.5% with a product purity of 99.5% was obtained.

We further studied the impact of pH and salt concentration and their interaction on recovery and purity of rHu GCSF produced using HEA Hypercel. It was observed that very low pH such as pH 5.1 results in significant decrease in recovery value which may be attributed to electrostatic repulsion of positively charged rHu GCSF molecule from the resin. Increase in the equilibration pH from 5.10 to 5.70 results in significant improvement in the protein recovery. The reason for the same can be attributed to the decrease in positive charge on rHu GCSF leading to suppression of the electrostatic repulsive interaction with the resin matrix. Further, the increase in salt concentration in the equilibration buffer helps in improving the recovery upto a certain level of salt concentration such as 300 mM, after which further increase in salt concentration results in a decrease in protein recovery. Stronger hydrophobic interaction at high salt concentration may be the reason for lower recovery of rHu GCSF. The operating pH and salt concentration for HEA Hypercel were 35 mM to 50 mM acetate with pH varying from 5 to 7 containing 0 mM to 300 mM sodium chloride, preferably 50 mM acetate with pH 5.5 containing 300 mM sodium chloride. Further, the elution strategy was based on a combination of decreasing pH and salt based gradient. A decrease in pH plays a role in increasing the positive charge on rHu GCSF leading to stronger electrostatic repulsion between the rHu GCSF molecule and the resin ligand. Similarly, decrease in salt concentration decreases the hydrophobic interaction between the protein molecule and the ligand. Table 2 shows the impact of varied pH and salt concentration and their interaction on recovery and purity of rHu GCSF produced using HEA Hypercel chromatography.

TABLE 2

Impact of different pH and salt concentration of equilibration buffer on recovery and purity of rHu GCSF

| S. No. | Equilibration buffer pH | Salt in mM | % Recovery in elution | % Purity |
| --- | --- | --- | --- | --- |
| 1 | 5.10 | 0 | 14.00 | 95.42 |
| 2 | 5.10 | 150 | 27.00 | 95.86 |
| 3 | 5.10 | 300 | 73.00 | 95.61 |
| 4 | 5.10 | 450 | 68.00 | 99.11 |
| 5 | 5.30 | 0 | 60.00 | 97.22 |
| 6 | 5.30 | 150 | 86.00 | 99.08 |
| 7 | 5.30 | 300 | 88.00 | 99.04 |
| 8 | 5.30 | 450 | 84.00 | 99.23 |
| 9 | 5.50 | 0 | 41.00 | 99.12 |
| 10 | 5.50 | 150 | 85.00 | 99.22 |
| 11 | 5.50 | 300 | 80.00 | 98.58 |
| 12 | 5.50 | 450 | 59.00 | 98.24 |
| 13 | 5.70 | 0 | 18.00 | 98.23 |
| 14 | 5.70 | 150 | 72.00 | 97.32 |
| 15 | 5.70 | 300 | 63.00 | 97.96 |
| 16 | 5.70 | 450 | 52.00 | 97.19 |

The elution step experiments were conducted using the 35 mM acetate buffer with pH ranging from 4 to 5 containing 0 mM to 100 mM sodium chloride concentration. It was observed that step elution without salt does not lead to significant improvement in the protein recovery. This indicates that salt plays a critical role in selective elution of rHu GCSF. It was observed that elution buffer comprising 50 mm acetate buffer at pH 4.00 containing 100 mM sodium chloride helped in achieving 89.26% of highly pure product (with methionine oxidized impurities less than 1% and reduced impurities less than 0.5%. Table 3 shows the impact of varied pH and salt concentrations of elution buffer on recovery and purity of rHu GCSF.

TABLE 3

Impact of different pH and salt (NaCl) concentration of elution buffer on recovery and purity of rHu GCSF

| S. No. | pH | NaCl molarity in mM | % Recovery | % Purity |
| --- | --- | --- | --- | --- |
| 1 | 4.3 | 20 | 82.64 | 91.62 |
| 2 | 4.3 | 60 | 88.88 | 92.89 |
| 3 | 4.3 | 100 | 89.26 | 99.16 |
| 4 | 4.7 | 20 | 90.21 | 94.57 |
| 5 | 4.7 | 60 | 92.54 | 96.57 |
| 6 | 4.7 | 100 | 93.2 | 96.77 |

In another embodiment of the invention binding of rHu GCSF to multimodal chromatographic resin was achieved in presence of chaotropic agent urea. In yet another embodiment of the invention binding of rHu GCSF to multimodal chromatographic resin was achieved in presence of arginine.

The present invention further provides a process for purification of recombinant protein, the process comprising solubilizing recombinant protein obtained from recombinant cell, refolding the solubilized recombinant protein, ultra-filtering and adjusting the pH of recombinant protein to obtain concentrated recombinant protein, and subjecting the concentrated recombinant protein to multimodal chromatography purification. In an embodiment of the present invention, the recombinant protein is either rHu GCSF.

An embodiment of the present invention provided a method of purifying recombinant human granulocyte colony stimulating factor (rHU GCSF) from a recombinant host cell, wherein the method comprises: obtaining rHU GCSF from a recombinant host cell in the form of inclusion bodies; solubilizing inclusion bodies using a solubilization buffer to obtain solubilized rHU GCSF; refolding the solubilized rHU GCSF using a refolding buffer to obtain refolded rHU GCSF; concentrating the refolded rHU GCSF by ultra-filtration to obtain concentrated rHU GCSF; subjecting the concentrated rHU GCSF to aqueous two phase extraction to remove host cell proteins and host cell DNA and to obtain rHU GCSF partition into polymeric phase and in the form of precipitate between the two aqueous phases; resolubilizing the rHU GCSF using a resulobilization buffer to obtain rHU GCSF solution; and subjecting the rHU GCSF solution to chromatography purification to remove product related impurities and obtain purified rHU GCSF.

In an embodiment of the present invention, there is provided a method of purifying recombinant human granulocyte colony stimulating factor (rHU GCSF) from a recombinant host cell, wherein the method comprises: obtaining rHU GCSF from a recombinant host cell in the form of inclusion bodies; solubilizing inclusion bodies using a solubilization buffer to obtain solubilized rHU GCSF; refolding the solubilized rHU GCSF using a refolding buffer to obtain refolded rHU GCSF; concentrating the refolded rHU GCSF by ultra-filtration to obtain concentrated rHU GCSF; and subjecting the concentrated rHU GCSF to multimodal chromatography to remove product related impurities, host cell proteins, and host cell nucleic acids and obtain purified rHU GCSF.

In another embodiment of the present invention, there is provided a method for purifying rHU GCSF from a recombinant host cell, wherein the recombinant host cell is *E. coli*.

In yet embodiment of the present invention, there is provided a method for purifying rHU GCSF from a recombinant host cell, wherein the solubilization buffer comprises a combination of chaotropic reagent and reducing agent.

In still another embodiment of the present invention, there is provided a method for purifying rHU GCSF from a recombinant host cell, wherein the chaotropic reagent is either urea or guanidium hydrochloride salts preferably urea.

Another embodiment of the present invention provides a method for purifying rHU GCSF from a recombinant host cell, wherein the reducing agent is selected from the group consisting of dithiothreitol, beta mercaptoethanol, and sodium borohydride preferably dithiothreitol.

In another embodiment of the present invention, there is provided a method for purifying rHU GCSF from a recombinant host cell, wherein the refolding buffer comprises components selected from the group consisting of tris, urea, arginine, ethylenediaminetetraacetic acid, histidine, sodium phosphate, potassium phosphate, and combinations thereof.

Another embodiment of the present invention provides a method for purifying rHU GCSF from a recombinant host cell, wherein the refolding buffer additionally comprises redox couple reagent.

In yet another embodiment of the present invention, there is provided a method for purifying rHU GCSF from a recombinant host cell, wherein the redox couple reagent is selected from the group consisting of cysteine and cystine, cystamine and cystamine, and oxidized glutathione and reduced glutathione, preferably cysteine and cystine.

In still another embodiment of the present invention, there is provided a method for purifying recombinant human granulocyte colony stimulating factor (rHU GCSF) from a recombinant host cell, wherein the ultra-filtration step further comprises adjusting pH of the concentrated rHU GCSF.

Another embodiment of the present invention provides a method for purifying recombinant human granulocyte colony stimulating factor (rHU GCSF) from a recombinant host cell, wherein the pH lies in the range of 3.00 to 5.70.

In another embodiment of the present invention, there is provided a method for purifying recombinant human granulocyte colony stimulating factor (rHU GCSF) from a recombinant host cell, wherein the aqueous two phase extraction is carried out by mixing polymer and salt to the concentrated rHu GCSF, wherein the polymer concentration is in the range of 7.5% to 15.5% and the salt concentration is in the range of 7.5% to 15.5%.

In another embodiment of the present invention, there is provided a method for purifying recombinant human granulocyte colony stimulating factor (rHU GCSF) from a recombinant host cell, wherein the aqueous two phase extraction is carried out by mixing polymer and salt to the concentrated rHu GCSF, wherein the polymer concentration is in the range of 7.5% to 15.5% (w/w) and the salt concentration is in the range of 7.5% to 15.5% (w/w).

In yet another embodiment of the present invention, there is provided a method for purifying recombinant human granulocyte colony stimulating factor (rHU GCSF) from a recombinant host cell, wherein the polymer is either ethylene oxide-propylene oxide copolymer or polyethylene glycol.

In still another embodiment of the present invention, there is provided a method for purifying recombinant human granulocyte colony stimulating factor (rHU GCSF) from a recombinant host cell, wherein the salt is selected from the group consisting of sodium phosphate, potassium phosphate, sodium sulphate, calcium sulphate, ammonium sulphate, ammonium phosphate, manganese sulphate, manganese phosphate, and calcium phosphate.

In another embodiment of the present invention, there is provided a method for purifying recombinant human granulocyte colony stimulating factor (rHU GCSF) from a recombinant host cell, wherein the resulobilization buffer comprises acetate, polysorbate, sorbitol, urea, and arginine.

Another embodiment of the present invention provides a method for purifying recombinant human granulocyte colony stimulating factor (rHU GCSF) from a recombinant host cell, wherein the product related impurities are methionine oxidized form of rHu GCSF, reduced form of rHu GCSF, and aggregated form of rHu GCSF.

Another embodiment of the present invention provides a method for purifying recombinant human granulocyte colony stimulating factor (rHU GCSF) from a recombinant host cell, wherein the chromatography purification is carried out by a method selected from the group consisting of ion exchange chromatography, hydrophobic chromatography, and multimodal chromatography.

Another embodiment of the present invention provides a method for purifying recombinant human granulocyte colony stimulating factor (rHU GCSF) from a recombinant host cell, wherein the chromatography purification is carried out by multimodal chromatography.

In another embodiment of the present invention, there is provided a method for purifying recombinant human granulocyte colony stimulating factor (rHU GCSF) from a recombinant host cell, wherein the multimodal chromatography purification comprises: binding the rHu GCSF to multimodal chromatography resin with a buffer comprising 10 mM to 100 mM acetate and 0 mM to 450 mM sodium chloride with the buffer pH lying in the range of 4.50 to 5.70; washing the multimodal chromatography resin with a buffer comprising 10 mM to 50 mM acetate and 0 mM to 450 mM sodium chloride with the buffer pH lying in the range of 4.50 to 5.70 to remove unbound protein and host related impurities, wherein the host related impurities are host cell proteins and host cell nucleic acids; eluting the rHu GCSF using an elution buffer comprising 10 mM to 50 mM acetate at pH ranging from 3 to 4.3 and 0 mM to 100 mM sodium chloride to obtain purified rHU GCSF, wherein the purified rHu GCSF has less than 1% methionine oxidized form of rHu GCSF, less than 0.5% reduced form of rHu GCSF, and less than 0.2% aggregated form of rHu GCSF.

In another embodiment of the present invention, there is provided a method for purifying recombinant human granulocyte colony stimulating factor (rHU GCSF) from a recombinant host cell, wherein the multimodal chromatography purification comprises: binding the rHu GCSF to multimodal chromatography resin with a buffer comprising 10 mM to 100 mM acetate preferably 50 mM acetate and 0 mM to 450 mM sodium chloride preferably 300 mM sodium chloride with the buffer pH lying in the range of 4.50 to 5.70 preferably 5.50; washing the multimodal chromatography resin with a buffer comprising 10 mM to 50 mM acetate and 0 mM to 450 mM sodium chloride with the buffer pH lying in the range of 4.50 to 5.70 to remove unbound protein and host related impurities, wherein the host related impurities are host cell proteins and host cell nucleic acids; eluting the rHu GCSF using an elution buffer comprising 10 mM to 50 mM acetate preferably 50 mM at pH ranging from 3.00 to 4.30 preferably 4.30 and 0 mM to 100 mM sodium chloride preferably 100 mM to obtain purified rHU GCSF, wherein the purified rHu GCSF has less than 1% methionine oxidized form of rHu GCSF, less than 0.5% reduced form of rHu GCSF, and less than 0.2% aggregated form of rHu GCSF.

In yet another embodiment of the present invention, there is provided a method for purifying recombinant human granulocyte colony stimulating factor (rHU GCSF) from a recombinant host cell, wherein the multimodal chromatography resin is selected from the group consisting of HEA Hypercel, Capto MMC, PPA Hypercel, Capto Adhere, MEP Hypercel, and Ceramic Hydroxyapatite.

In still another embodiment of the present invention, there is provided a method for purifying recombinant human granulocyte colony stimulating factor (rHU GCSF) from a recombinant host cell, wherein the binding of rHu GCSF to multimodal chromatography resin is carried out a pH less than pKa of the multimodal chromatography resin ligand.

Another embodiment of the present invention provides a method for purifying recombinant human granulocyte colony stimulating factor (rHU GCSF) from a recombinant host cell, wherein the elution of rHu GCSF is carried out using combined pH and salt based step elution.

Another embodiment of the present invention provides a pharmaceutical composition comprising the purified rHu GCSF obtained from the method comprising: solubilizing inclusion bodies using a solubilization buffer to obtain solubilized rHU GCSF; refolding the solubilized rHU GCSF using a refolding buffer to obtain refolded rHU GCSF; concentrating the refolded rHU GCSF by ultra-filtration to obtain concentrated rHU GCSF; subjecting the concentrated rHU GCSF to aqueous two phase extraction to remove host cell proteins and host cell DNA and to obtain rHU GCSF partitioned into polymeric phase and in the form of precipitate between the two aqueous phases; resolubilizing the rHU GCSF using a resulobilization buffer to obtain rHU GCSF solution; and subjecting the rHU GCSF solution to chromatography purification to remove product related impurities and obtain purified rHU GCSF. and pharmaceutically acceptable carrier.

Another embodiment of the present invention provides a pharmaceutical composition comprising the purified rHu GCSF obtained from the method comprising: obtaining rHU GCSF from a recombinant host cell in the form of inclusion bodies; solubilizing inclusion bodies using a solubilization buffer to obtain solubilized rHU GCSF; refolding the solubilized rHU GCSF using a refolding buffer to obtain refolded rHU GCSF; concentrating the refolded rHU GCSF by ultra-filtration to obtain concentrated rHU GCSF; and subjecting the concentrated rHU GCSF to multimodal chromatography to remove product related impurities, host cell proteins, and host cell nucleic acids and obtain purified rHU GCSF.

Although the subject matter has been described in considerable detail with reference to certain preferred embodiments thereof, other embodiments are possible. As such, the spirit and scope of the appended claims should not be limited to the description of the preferred embodiment contained therein.

EXAMPLES

The disclosure will now be illustrated with working examples, which are intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1

Purification of rHu GCSF rHu GCSF was purified by the following steps as mentioned below.

Solubilization of the Inclusion Bodies rHu GCSF was obtained in the inclusion bodies from the recombinant cells expressing rHu GCSF. 1.15 grams of inclusion bodies was dissolved in 100 ml of solubilization buffer (concentration 11.5 mg/ml, 50 mM Tris, 6M Urea). Inclusion bodies were solubilized by using magnetic stirrer for 45 minutes at a temperature of 25° C., centrifuged at 7000 rpm for 10 minutes and filtered using filter paper of pore size 1 µm. The OD of the solubilized inclusion bodies was adjusted between 0.45±0.3.

Dithiothreitol (DTT) was added as the reducing agent such that the concentration of dithiothreitol (1.34M) in solubilization buffer was 10 mM and 1 mM in final refold (153 mg for 100 ml solubilized inclusion bodies). The solution was kept under stirring condition at room temperature (25° C.) for 30 minutes for reduction. The pH of the reduced inclusion bodies was adjusted to 10.0 using 2M NaOH.

Refolding of the Solubilized Inclusion Bodies 895 ml of refolding buffer (comprising 50 mM tris, 5% sorbitol, and total made up to 1000 ml milli Q water) was taken in the refolding vessel. 0.625 gm of cystine dihydrochloride solution was added to it. The pH of this solution was adjusted to 10.0 using 2M NaOH and the total volume was made up to 900 ml. The inclusion bodies solution was diluted at the rate of 5 ml/min over the period of 20 minutes with cysteine.

Ultrafiltration and pH Adjustment of the Refolded Protein

After the refolding of rHu GCSF, protein was concentrated by ultra-filtration. The pH of the concentrated protein sample was then adjusted to pH 4.00. The protein sample was then centrifuged at 8000 rpm (4° C.) for 30 minutes and the supernatant used as an input for aqueous two phase extraction step.

Aqueous Two Phase Extraction for Isolation of Various Process Related Impurities Two phase system was formed by adding appropriate amount of polymer PEG 6000 for a final solution concentration of 11.5% (w/w), anhydrous sodium sulphate salt for a final concentration of 9.5% (w/w) and protein solution (1.5 mg/ml) in a 15 ml falcon tube. The total mass of the system was made up to 12 grams. The solution was then mixed on a rocker shaker for 10 minutes and was left undisturbed for gravity settling for 3 hours.

The addition of the phase forming components to the protein solution led to formation of two phases. In forward extraction, a combination of hydrophobic, salting out and electrostatic interaction leads to precipitation of the target product at interface. A thick layer of precipitate containing rHu GCSF was observed at the interface of the two aqueous phases.

Resulobilization of the Precipitate

The precipitate formed during the forward extraction step was recovered by carefully removing the bottom phase with the help of a syringe and needle. The protein precipitate was recovered along with the top polymer phase. Further, the recovered protein precipitate was solubilized using resulobilization buffer comprising acetate buffer pH 4.0, 0.1 mg/ml polysorbate, 5% sorbitol, 1M urea and 0.5M arginine. The pH of the resolubilizing buffer was adjusted to pH 5.70 using glacial acetic acid. 6 ml of resolubilizing buffer was used for 4 ml of aqueous two phase extraction output. The mixture was then left for shaking on a rocker shaker for about 10 minutes. The combination of urea and arginine led to an effective resolubilization of the protein precipitate, which was due to the cooperative effect of urea and arginine in breaking the different hydrophobic aggregates. Further, arginine also prevents the formation of soluble hydrophobic oligomers.

Following the resulobilization of the precipitate, the protein solution was centrifuged for 8 min at 8000 rpm at 4° C. The supernatant was then used as the feed for multimodal chromatography purification.

Structural and Functional Characterization of Resolubilized Precipitate of rHu GCSF Structural and functional integrity of resolubilized rHu GCSF was confirmed using various analytical tools and the in-vitro bioassay.

Intact Mass Analysis and Peptide Mapping by UPLC-MS

Structural integrity of the rHu GCSF after resolubilization was confirmed using intact mass analysis as well as peptide mapping. UPLC based separation was achieved using H-Class Bio UPLC chromatographic system sold under the trademark ACQUITY UPLC® (from Waters Corporation Milford, Mass., USA) followed by MS analysis with the High Definition Mass Spectrometry (HDMS) system sold under the trademark SYNAPT® G2-S HDMS (from Waters Corporation Milford, Mass., USA). Data processing for determination of intact mass as well as quantification of host cell protein was performed using application managing software sold under the trademark Waters® BIOPHARMALYNX™ 1.3.2 and proteomics research platform sold under the trademark PROTEINLYNX GLOBAL SERVER™ (PLGS) 2.5.2 (from Waters Corporation Milford, Mass., USA). For intact mass analysis BEH300, C4 column (2.1×50 mm, Waters Corporation Milford, Mass., USA, Catalogue No. 1860036850 was used with a linear gradient: 5-90% B in 3.5 min with buffer A being 0.1% fluoroacetic acid (FA) in water and buffer B being 0.1% FA in ACN. LC/MS based peptide mapping analysis of reduced and non-reduced digest (S—S bond mapping) of rHu GCSF was preformed to verify the amino acid sequence and possible structural modification during rHu GCSF processing. Digestion under non reducing conditions was performed using sequence-grade GluC (1:20 w/w) by incubating at 37° C. in 100 mM Tris buffer, pH 7.5 for 4 hours. Before digestion, protein was denatured in 8.0M guanidine hydrochloride in 250 mM Trizma hydrochloride buffer, pH 7.5, alkylated with 6 mM IAA (20 minutes, in dark), and buffer exchanged to 100 mM Trizma hydrochloride buffer, pH 7.5. For reduced digestion, non-reduced rHu GCSF digest was reduced with 3 mM DTT (for 45 minutes) and alkylated with 6MM IAA for 20 minutes in the dark.

Intact mass analysis and peptide mapping using LC-MS showed mass integrity as well as presence of correct disulphide linkages in the resolubilized rHu GCSF. The results proved the absence of any structural distortion of rHu GCSF during the resolubilized of rHu GCSF. LC/MSE peptide mapping of the reduced and non-reduced digests confirmed the amino acid sequence of GCSF with an additional N-terminus methionine and the S—S linkages. The S—S linkages identified within the GCSF protein are: between cystines at positions 37 and 43 and between cystines at positions 65 and 75. Fragment ions from the single LC/MSE run provided both sequence conformation and sites of cystines and N-terminal methionine residue.

Size Exclusion Chromatography (SEC)-HPLC Analysis

Figure 1A:
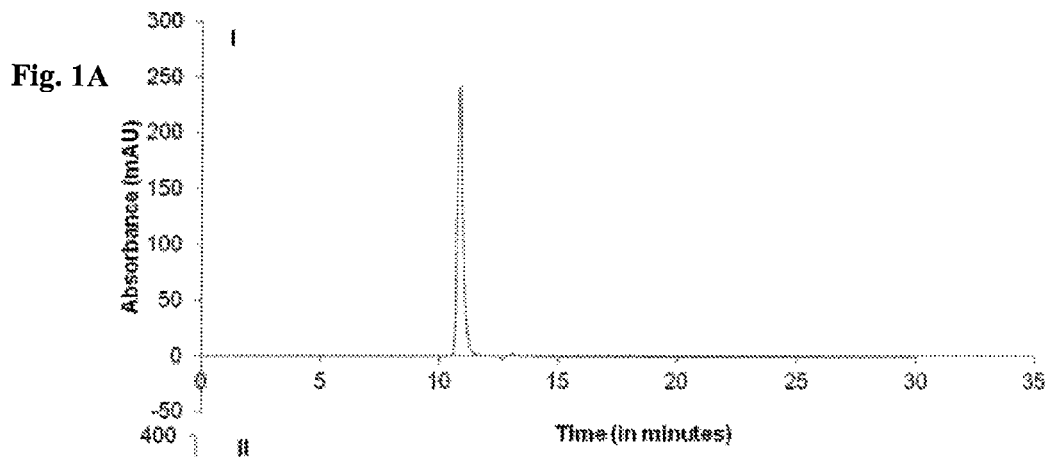
FIG. 1A is a Chromatogram for standard GCSF, showing the structural characterization of resolubilized GCSF, and size exclusion chromatography to show absence of any aggregates.

Aggregate content in the process output was determined using SEC-HPLC analysis performed using Tosho TSK 3000 SW XL 7.8×300 mm (Tosoh Bioscience LLC, Part No. 08541, King of Prussia, Pa. USA) column. The mobile phase consisted of 100 mM ammonium hydrogen carbonate, pH 7.00 buffer. Analysis was done in isocratic mode with 0.5 ml/min flow rate at 30° C. Protein detection was performed using a photo diode array detector at 215 nm. Size exclusion chromatography analysis confirmed the absence of aggregates in the resolubilized rHu GCSF (FIG. 1A).

CD Spectroscopy

Secondary structure of rHu GCSF was determined by CD spectroscopy. Sample with 0.2 mg/ml of resolubilized rHu GCSF was taken into the respective buffer in a 2 mm path length cuvette and far UV CD spectrum was measured from 250-200 nm in a JASCO J-815 Spectropolarimeter (Jasco, Inc. Mary's Court, Easton, Md. 21601 USA.) with the spectral band width of 5 nm. An average of three scans was plotted against the wavelength. CD spectroscopy confirmed the structural integrity of the alpha helical structure of the resolubilized rHu GCSF.

SDS PAGE and 2D Gel Electrophoresis Analysis

SDS PAGE was used for identification of the high and low molecular weight impurities associated with rHu GCSF. A 1 mm thick resolving polyacrylamide gel (13%) was used under non reducing condition and constant voltage. Each sample was boiled for 5 min in the starting buffer before being loaded into the gel. Silver staining was used to detect proteins after electrophoretic separation. 2 D gel electrophoresis was used for identification of isoelectric points and molecular weights of the HCP. *E. coli* extract was suspended in rehydration buffer containing 10 mM DTT and subjected to 2-D gel electrophoresis with the first dimension in 7 cm pH 3-10 IPG strip and the second dimension in 10% SDS PAGE. SDS PAGE analysis confirmed the structural integrity of the alpha helical structure of the resolubilized rHu GCSF.

Bioassay of rHu GCSF

Bioactivity of resolubilized rHu GCSF was determined using the myeloid leukemic cell line. NFS-60, a myeloid murine leukaemia cell line, was maintained in RPMI 1640 medium supplemented with 10% foetal calf serum. Cells were maintained in a humid atmosphere, with a composition of air-CO2 (95:5), in 50-ml polystyrene Nunclon Delta flasks (A/S Nunc, Roskilde, Denmark) and split three times per week. About 50 µl of suspension containing $7.0 \times 10^5$ cells per ml was added into each well of the 96 well flat-bottomed microtiter plates. To the each well containing 50 µl of cell suspension, 50 µl of the test solution was added in triplicates. Assay includes eight working dilutions from 800 IU/ml to 6.25 IU/ml of reference standard and test samples. Plates were then incubated at 37° C. for 48 h in a humidified incubator using 6±1% CO2. After 48 hours incubation 20 µl solution of 5.0 g/l solution of Tetrazolium salt was added to each well. The reaction was allowed to proceed during 4 h in an incubator. This cytochemical stain is converted by cellular dehydrogenases to a colored formazan product which was further quantified using colorimetric method by measuring absorbance value at 490 nm. Data analysis for determination of the potency of the samples was carried out using Combistat parallel cell line assay.

In-vitro bioassay confirmed the biological activity of the resolubilized rHu GCSF. rHu GCSF rHu GCSF produced using the developed platform showed 85.4% of biological potency in comparison with the marketed product Neukine. These experiments confirmed that resulobilization of interfacial precipitate does not lead to any structural or functional alteration in the biological activity of the rHu GCSF.

Chromatographic Purification of Resolubilized Precipitate

The resolubilized precipitate was subjected to chromatographic purification selected from the group comprising ion exchange chromatography, hydrophobic chromatography, multimodal chromatography or their combination. The chromatographic purification of the resolubilized precipitate by multimodal chromatography is described below.

Multimodal Chromatographic Purification of Resolubilized Precipitate

Figure 2:
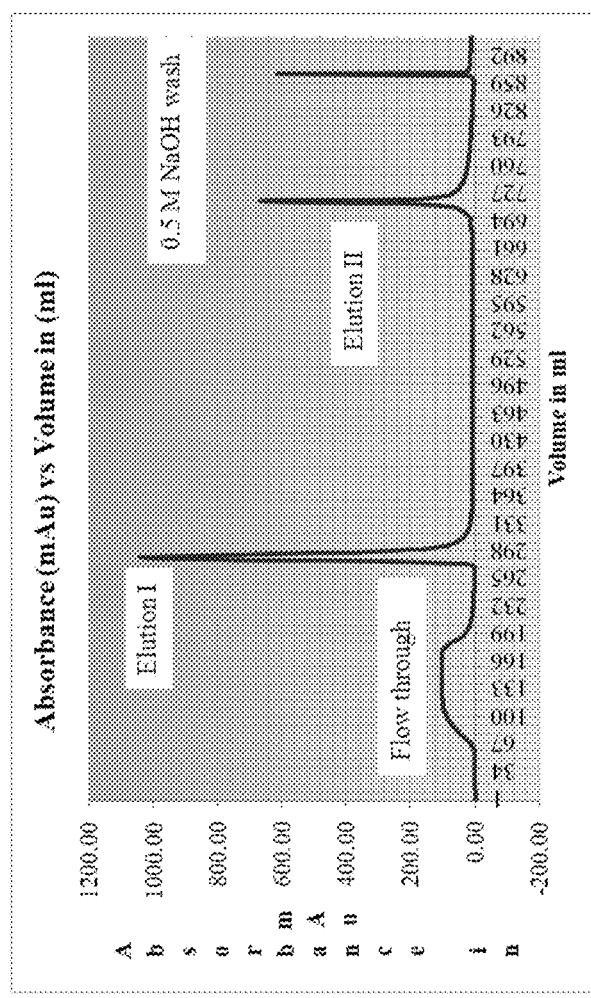
FIG. 2 shows the chromatogram obtained for the multimodal chromatography purification.

The multimodal chromatography purification was carried out by using the below mentioned components.
Column: HEA Hypercel Prepacked 1.00 ml columns or PPA Hypercel Prepacked 1.00 ml columns
Equilibration buffer: 50 mM acetate at pH 5.50 and 300 mM NaCl
Elution buffer I: 50 mM acetate at pH 4.3 and 100 mm NaCl
Elution buffer II: 100 mM citrate at pH 3.00
Load volume: 10.00 ml Multimodal chromatography was performed using an ÄKTA Purifier chromatography system (GE Healthcare BioSciences, Uppsala, Sweden). Chromatography experiments involving HEA or PPA Hypercel resins were performed using prepacked 1 ml column (5 mm ID×50 mm from Pall Life sciences USA). Chromatography column was equilibrated using the selected equilibration buffer (5-10 CV). Pretreated GCSF protein solution was then injected into the chromatography column using a sample pump (GE Healthcare BioSciences). After sample loading unbound protein sample was removed using equilibration buffer wash step (5 CV). Elution step involves selective salt or pH based elution gradient. The output from the chromatography column was by UV detection at 280, 260 and 215 nm. FIG. 2 shows the chromatogram after the multimodal chromatography was carried out for the purification of rHu GCSF. The purified rHu GCSF was obtained in elution I. The elution II fraction consists of product related impurities.

We preformed the multimodal chromatography with few other equilibration buffers and elution buffers I. The process for carrying out the procedure of multimodal chromatography remained the same as described above, with changes in the equilibration buffer and elution buffer 1.

The different equilibration buffers used for multimodal chromatography are mentioned below:
50 mM acetate at pH 5.70
50 mM acetate at pH 5.70 and 300 mM NaCl
50 mM acetate at pH 5.50 and 150 mM NaCl
50 mM acetate at pH 5.50 and 300 mm NaCl The different elution buffer 1 used for multimodal chromatography are mentioned below:
35 mM acetate at pH 4.3
50 mM acetate at pH 4.00 and 100 mM NaCl
50 mM acetate at pH 4.7 and 100 mM NaCl Biophysical Characterization of rHu GCSF Produced Using Multimodal Chromatography The biophysical characterization of rHu GCSF was done using various analytical tools and in-vitro bioassay.

SDS PAGE and 2D Gel Electrophoresis Analysis

SDS PAGE was used for identification of the high and low molecular weight impurities associated with rHu GCSF. A 1 mm thick resolving polyacrylamide gel (13%) was used under non reducing condition and constant voltage. Each sample was boiled for 5 minutes in the starting buffer before being loaded into the gel. Silver staining was used to detect proteins after electrophoretic separation. 2 D gel electrophoresis was used for identification of isoelectric points and molecular weights of the HCP. E. coli extract was suspended in rehydration buffer containing 10 mM DTT and subjected to 2-D gel electrophoresis with the first dimension in 7 cm pH 3-10 IPG strip and the second dimension in 10% SDS PAGE. Quality of the product was verified using SDS PAGE analysis and was found in good agreement with that of standard GCSF (FIG. 3). Lanes B and C of FIG. 3 depict the purified rHu GCSF which was characterized using SDS PAGE. The size of the purified RHu GCSF was same as that of the standard GCSF shown in Lane D.

Intact Mass Analysis and Peptide Mapping by UPLC-MS

Structural integrity of the GCSF after resolublization was also confirmed using intact mass analysis as well as peptide mapping. UPLC based separation was achieved using H-Class Bio ACQUITY® UPLC® (from Waters Corporation Milford, Mass. USA) followed by MS analysis with Synapt G2-S HDMS (from Waters Corporation Milford, Mass. USA). Data processing for determination of intact mass as well as quantification of HCP was performed using BiopharmaLynx™ 1.3.2 and PLGS 2.5.2. (Waters Corporation Milford, Mass. USA). For intact mass analysis BEH300, C4 column (2.1×50 mm, Waters Corporation Milford, Mass. USA, Catalogue No. 186003685) was used with a linear gradient: 5-90% B in 3.5 min with buffer A being 0.1% fluoroacetic acid (FA) in Water and buffer B being 0.1% FA in ACN. LC/MS based peptide mapping analyses of reduced and non reduced digest (S—S bond mapping) of GCSF were performed to verify the amino acid sequence and possible structural modification during GCSF processing. Digestion under non reducing conditions was performed using sequence-grade GluC (1:20 w/w) by incubating at 37° C. in 100 mM Tris buffer, pH 7.5 for 4 hours. Before digestion, protein was denatured in 8.0 M guanidine hydrochloride in 250 mM Trizma hydrochloride buffer, pH 7.5, alkylated with 6 mM IAA (20 min, in dark), and buffer exchanged to 100 mM Trizma hydrochloride buffer, pH 7.5. For reduced digestion, non-reduced G-CSF digest was reduced with 3 mM DTT (45 min) and alkylated with 6 mM IAA for 20 minutes in the dark.

Intact mass analysis and peptide mapping using LC-MS analysis of GCSF produced using multimodal chromatography showed mass integrity as well as presence of correct disulphide linkages which further demonstrates the lack of any structural distortion during multimodal chromatographic purification of GCSF. An intact mass analysis showed that the process output contains GCSF protein as the main component with an additional N-terminal methionine residue in the sequence, and was not glycosylated. LC/MSE peptide mapping analyses of reduced and non-reduced digests confirmed the amino acid sequence of GCSF with an additional N-terminal methionine and the S—S linkages. The S—S linkages identified within the GCSF protein are: between cystines at positions 37 and 43 and between cystines at positions 65 and 75. FIG. 5 compares the intact mass as well as peptide map of the GCSF produced using multimodal chromatography platform with Neukine (GCSF formulation marketed by Intas Biopharmaceuticals Ltd.). Good agreement of the observed results confirms the bio similarity of the developed product.

Bioassay of rHu GCSF

Bioactivity of rHu GCSF was determined using the myeloid leukemic cell line. NFS-60, a myeloid murine leukaemia cell line, was maintained in RPMI 1640 medium supplemented with 10% foetal calf serum. Cells were maintained in a humid atmosphere, with a composition of air-$CO_2$ (95:5), in 50-ml polystyrene Nunclon Delta flasks (A/S Nunc, Roskilde, Denmark) and split three times per week. About 50 µl of suspension containing $7.0 \times 10^5$ cells per ml was added into each well of the 96 well flat-bottomed microtiter plates. To the each well containing 50 µl of cell suspension, 50 µl of the test solution was added in triplicates. Assay includes eight working dilutions from 800 IU/ml to 6.25 IU/ml of reference standard and test samples. Plates were then incubated at 37° C. for 48 h in a humidified incubator using 6±% $CO_2$. After 48 hours incubation 20 µl solution of 5.0 g/l solution of Tetrazolium salt was added to each well. The reaction was allowed to proceed during 4 h in an incubator. This cytochemical stain is converted by cellular dehydrogenases to a colored formazan product which was further quantified using colorimetric method by measuring absorbance value at 490 nm. Data analysis for determination of the potency of the samples was carried out using Combistat parallel cell line assay. Invitro bioassay confirms the biological activity of resolubilized GCSF. GCSF produced using the developed platform showed 89.3% of biological potency compared to Neukine. This confirms that developed chromatography step of the present invention does not lead to any structural or functional alteration in the biological activity of the GCSF protein.

Example 2

Purification of rHu GCSF
rHu GCSF was purified by the following steps as mentioned below.
Solubilization of the Inclusion Bodies
rHu GCSF was obtained in the inclusion bodies from the recombinant cells expressing rHU GCSF. 1.15 grams of inclusion bodies was dissolved in 100 ml of solubilization buffer (concentration 11.5 mg/ml, 50 mM Tris, 6M Urea). Inclusion bodies were solubilized by using magnetic stirrer for 45 minutes at a temperature of 25° C., centrifuged at 7000 rpm for 10 minutes and filtered using filter paper of pore size 1 µm. The OD of the solubilized inclusion bodies was adjusted between 0.45±0.3.

Dithiothreitol (DTT) was added as the reducing agent such that the concentration of dithiothreitol (1.34M) in solubilization buffer was 10 mM and 1 mM in final refold (153 mg for 100 ml solubilized inclusion bodies). The solution was kept under stirring condition at room temperature (25° C.) for 30 minutes for reduction. The pH of the reduced inclusion bodies was adjusted to 10.0 using 2M NaOH.
Refolding of the Solubilized Inclusion Bodies
895 ml of refolding buffer (comprising 50 mM tris, 5% sorbitol, and total made up to 1000 ml milli Q water) was taken in the refolding vessel. 0.625 gm of cystine dihydrochloride solution was added to it. The pH of this solution was adjusted to 10.0 using 2M NaOH and the total volume was made up to 900 ml. The inclusion bodies solution was diluted at the rate of 5 ml/min over the period of 20 minutes with cysteine.
Ultrafiltration and pH Adjustment of the Refolded Protein
After the refolding of rHu GCSF, protein was concentrated by ultra-filtration using 3 kDa Minimate™ tangential flow filtration capsule. The pH of the concentrated protein sample was then adjusted to pH 4.00. The protein sample was then centrifuged at 8000 rpm (4° C.) for 30 minutes and the supernatant used as an input for aqueous two phase extraction step. Phase forming components were added to the pH adjusted protein solution.
Aqueous Two Phase Extraction for Isolation of Various Process Related Impurities
Two phase system was formed by adding appropriate amount of polymer PEG 6000 for a final solution concentration of 11.5% (w/w), anhydrous sodium sulphate salt for a final concentration of 7.5% (w/w) and 1.5 mg/ml of protein solution in a 15 ml falcon tube. The total mass of the system was made up to 12 grams. The solution was then mixed on a rocker shaker for 10 minutes and then the two phases were settled by centrifugation at 4000 rpm for 4 minutes at 4° C.

The addition of phase forming components to the protein solution led to the formation of two phases. In forward extraction, a combination of hydrophobic, salting out and electrostatic interaction leads to precipitation of the target product at interface.
Resulobilization of the Precipitate
The precipitate formed during the forward extraction step was recovered by carefully removing the bottom phase with the help of a syringe and needle. The protein precipitate was recovered along with the top polymer phase. Further, the recovered protein precipitate was solubilized using resulobilization buffer comprising of acetate buffer pH 4.0, 0.1 mg/ml polysorbate, 5% sorbitol, 2M urea and 0.5M arginine. The pH of the resolubilizing buffer was adjusted to pH 5.50 using glacial acetic acid. 6 ml of resolubilizing buffer was used for 4 ml of aqueous two phase extraction output. The mixture was then left for shaking on a rocker shaker for about 10 minutes. Following the resulobilization of the precipitate, protein solution was filtered using a 0.22 micron filter paper. The filtrate was then used as the feed for multimodal chromatography purification.
Structural and Functional Characterization of Resolubilized Precipitate of rHu GCSF
Structural and functional integrity of resolubilized rHu GCSF was confirmed using various analytical tools and the in-vitro bioassay.
Intact Mass Analysis and Peptide Mapping by UPLC-MS
Structural integrity of the rHu GCSF after resolubilization was confirmed using intact mass analysis as well as peptide mapping. UPLC based separation was achieved using H-Class Bio UPLC chromatographic system sold under the trademark ACQUITY UPLC® (from Waters Corporation Milford, Mass., USA) followed by MS analysis with the High Definition Mass Spectrometry (HDMS) system sold under the trademark SYNAPT® G2-S HDMS (from Waters Corporation Milford, Mass., USA). Data processing for determination of intact mass as well as quantification of host cell protein was performed using application managing software sold under the trademark Waters® BIOPHARMALYNX™ 1.3.2 and proteomics research platform sold under the trademark PROTEINLYNX GLOBAL SERVER™ (PLGS) 2.5.2 (from Waters Corporation Milford, Mass., USA). For intact mass analysis BEH300, C4 column (2.1×50 mm, Waters Corporation Milford, Mass., USA, Catalogue No. 1860036850 was used with a linear gradient: 5-90% B in 3.5 min with buffer A being 0.1% fluoroacetic acid (FA) in water and buffer B being 0.1% FA in ACN. LC/MS based peptide mapping analysis of reduced and non-reduced digest (S—S bond mapping) of rHu GCSF was preformed to verify the ammo acid sequence and possible structural modification during rHu GCSF processing. Digestion under non reducing conditions was performed using sequence-grade GluC (1:20 w/w) by incubating at 37° C. in 100 mM Tris buffer, pH 7.5 for 4 hours. Before digestion, protein was denatured in 8.0M guanidine hydrochloride in 250 mM Trizma hydrochloride buffer, pH 7.5, alkylated with 6 mM IAA (20 minutes, in dark), and buffer exchanged to 100 mM Trizma hydrochloride buffer, pH 7.5. For reduced digestion, non-reduced rHU GCSF digest was reduced with 3 mM DTT (for 45 minutes) and alkylated with 6MM IAA for 20 minutes in the dark.

Intact mass analysis and peptide mapping using LC-MS showed mass integrity as well as presence of correct disulphide linkages in the resolubilized rHu GCSF. The results proved the absence of any structural distortion of rHu GCSF during the resolubilized of rHu GCSF. LC/MSE peptide mapping of the reduced and non-reduced digests confirmed the amino acid sequence of GCSF with an additional N-terminus methionine and the S—S linkages. The S—S linkages identified within the GCSF protein are: between cystines at positions 37 and 43 and between cystines at positions 65 and 75. Fragment ions from the single LC/MSE run provided both sequence conformation and sites of cystines and N-terminal methionine residue.

Size Exclusion Chromatography (SEC)-HPLC Analysis

Aggregate content in the process output was determined using SEC-HPLC analysis performed using Tosho TSK 3000 SW XL 7.8×300 mm (Tosoh Bioscience LLC, Part No. 08541, King of Prussia, Pa. USA) column. The mobile phase consisted of 100 mM ammonium hydrogen carbonate, pH 7.00 buffer. Analysis was done in isocratic mode with 0.5 ml/min flow rate at 30° C. Protein detection was performed using a photo diode array detector at 215 nm. Size exclusion chromatography analysis confirmed the absence of aggregates in the resolubilized rHu GCSF (FIG. 1A).

CD Spectroscopy

Secondary structure of rHU GCSF was determined by CD spectroscopy. Sample with 0.2 mg/ml of resolubilized rHU GCSF was taken into the respective buffer in a 2 mm path length cuvette and far UV CD spectrum was measured from 250-200 nm in a JASCO J-815 Spectropolarimeter (Jasco, Inc. Mary's Court, Easton, Md. 21601 USA.) with the spectral band width of 5 nm. An average of three scans was plotted against the wavelength. CD spectroscopy confirmed the structural integrity of the alpha helical structure of the resolubilized rHu GCSF.

SDS PAGE and 2D Gel Electrophoresis Analysis

SDS PAGE was used for identification of the high and low molecular weight impurities associated with rHu GCSF. A 1 mm thick resolving polyacrylamide gel (13%) was used under non reducing condition and constant voltage. Each sample was boiled for 5 min in the starting buffer before being loaded into the gel. Silver staining was used to detect proteins after electrophoretic separation. 2 D gel electrophoresis was used for identification of isoelectric points and molecular weights of the HCP. E. coli extract was suspended in rehydration buffer containing 10 mM DTT and subjected to 2-D gel electrophoresis with the first dimension in 7 cm pH 3-10 IPG strip and the second dimension in 10% SDS PAGE.

Figure 1B:
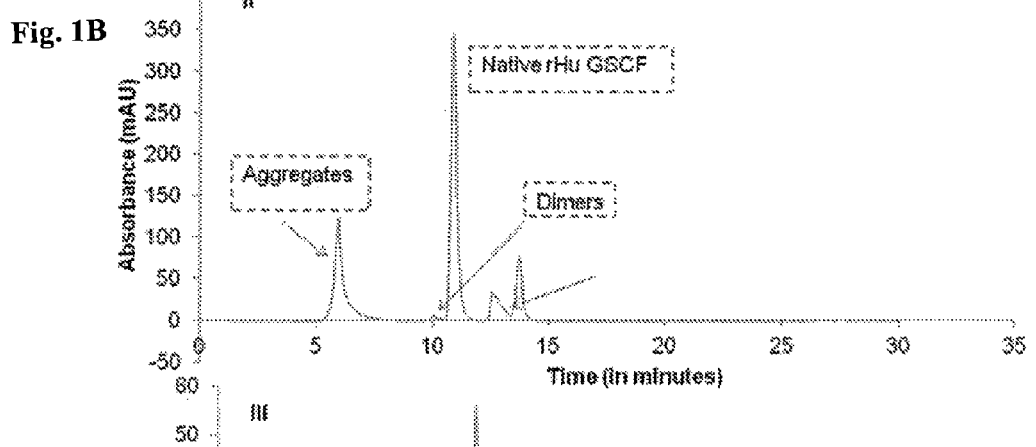
FIG. 1B is a Chromatogram for refolded protein used as the input, showing the structural characterization of resolubilized GCSF, and size exclusion chromatography to show absence of any aggregates.
Figure 1C:
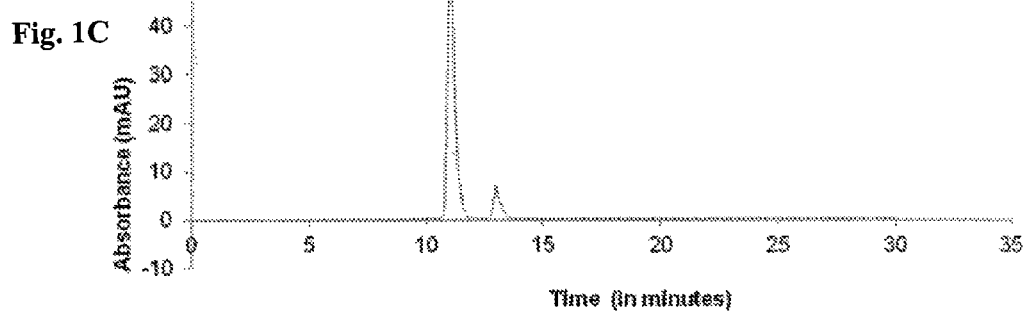
FIG. 1C is a Chromatogram for resolubilized GCSF produced using aqueous two phase purification), showing the structural characterization of resolubilized GCSF, and size exclusion chromatography to show absence of any aggregates.

SDS PAGE analysis confirmed the structural integrity of the alpha helical structure of the resolubilized rHu GCSF (FIG. 1B).

Bioassay of rHu GCSF

Bioactivity of resolubilized rHu GCSF was determined using the myeloid leukemic cell line. NFS-60, a myeloid murine leukaemia cell line, was maintained in RPMI 1640 medium supplemented with 10% foetal calf serum. Cells were maintained in a humid atmosphere, with a composition of air-CO2 (95:5), in 50-ml polystyrene Nunclon Delta flasks (A/S Nunc, Roskilde, Denmark) and split three times per week. About 50 µl of suspension containing $7.0 \times 10^5$ cells per ml was added into each well of the 96 well flat-bottomed microtiter plates. To the each well containing 50 µl of cell suspension, 50 µl of the test solution was added in triplicates. Assay includes eight working dilutions from 800 IU/ml to 6.25 IU/ml of reference standard and test samples. Plates were then incubated at 37° C. for 48 h in a humidified incubator using 6±1% CO2. After 48 hours incubation 20 µl solution of 5.0 g/l solution of Tetrazolium salt was added to each well. The reaction was allowed to proceed during 4 h in an incubator. This cytochemical stain is converted by cellular dehydrogenases to a colored formazan product which was further quantified using colorimetric method by measuring absorbance value at 490 nm. Data analysis for determination of the potency of the samples was carried out using Combistat parallel cell line assay.

In-vitro bioassay confirmed the biological activity of the resolubilized rHu GCSF. rHu GCSF rHu GCSF produced using the developed platform showed 85.4% of biological potency in comparison with the marketed product Neukine. These experiments confirmed that resulobilization of interfacial precipitate does not lead to any structural or functional alteration in the biological activity of the rHu GCSF.

Chromatographic Purification of Resolubilized Precipitate

The resolubilized precipitate was subjected to chromatographic purification selected from the group comprising ion exchange chromatography, hydrophobic chromatography, multimodal chromatography or their combination. The chromatographic purification of the resolubilized precipitate by multimodal chromatography is described below.

Multimodal Chromatographic Purification of Resolubilized Precipitate

The multimodal chromatography purification was carried out by using the below mentioned components.

Column: HEA Hypercel Prepacked 1.00 ml columns or PPA Hypercel Prepacked 1.00 ml columns Equilibration buffer: 50 mM acetate at pH 5.50 and 300 mM NaCl Elution buffer I: 50 mM acetate at pH 4.3 and 100 mm NaCl Elution buffer II: 100 mM citrate at pH 3.00

Load volume: 10.00 ml

Multimodal chromatography was performed using an ÄKTA Purifier chromatography system (GE Healthcare Bio-Sciences, Uppsala, Sweden). Chromatography experiments involving HEA or PPA Hypercel resins were performed using prepacked 1 ml column (5 mm ID×50 mm from Pall Life sciences USA). Chromatography column was equilibrated using the selected equilibration buffer (5-10 CV). Pretreated GCSF protein solution was then injected into the chromatography column using a sample pump (GE Healthcare Bio-Sciences). After sample loading unbound protein sample was removed using equilibration buffer wash step (5 CV). Elution step involves selective salt or pH based elution gradient. The output from the chromatography column was monitored using pH, conductivity and UV detection at 280, 260 and 215 nm. FIG. 2 shows the chromatogram for the multimodal chromatography carried out for the purification of rHu GCSF.

We preformed the multimodal chromatography with few other equilibration buffers and elution buffers I. The process for carrying out the procedure of multimodal chromatography remained the same as described above, with changes in the equilibration buffer and elution buffer 1.

The different equilibration buffers used for multimodal chromatography are mentioned below:

50 mM acetate at pH 5.70

50 mM acetate at pH 5.70 and 300 mM NaCl 50 mM acetate at pH 5.50 and 150 mM NaCl 50 mM acetate at pH 5.50 and 300 mm NaCl The different elution buffer 1 used for multimodal chromatography are mentioned below:

35 mM acetate at pH 4.3

50 mM acetate at pH 4.00 and 100 mM NaCl 50 mM acetate at pH 4.7 and 100 mM NaCl Biophysical Characterization of rHu GCSF Produced Using Multimodal Chromatography The biophysical characterization of rHu GCSF was done using various analytical tools and in-vitro bioassay as described in Example 1.

Example 3

Purification of rHu GCSF rHu GCSF was purified by the following steps as mentioned below.

Solubilization of the Inclusion Bodies rHu GCSF was obtained in the inclusion bodies from the recombinant cells expressing rHU GCSF. 1.15 grams of inclusion bodies was dissolved in 100 ml of solubilization buffer (concentration 11.5 mg/ml, 50 mM Tris, 6M Urea). Inclusion bodies were solubilized by using magnetic stirrer for 45 minutes at a temperature of 25° C., centrifuged at 7000 rpm for 10 minutes and filtered using filter paper of pore size 1 μm. The OD of the solubilized inclusion bodies was adjusted between 0.45±0.3.

Dithiothreitol (DTT) was added as the reducing agent such that the concentration of dithiothreitol (1.34M) in solubilization buffer was 10 mM and 1 mM in final refold (153 mg for 100 ml solubilized inclusion bodies). The solution was kept under stirring condition at room temperature (25° C.) for 30 minutes for reduction. The pH of the reduced inclusion bodies was adjusted to 10.0 using 2M NaOH.

Refolding of the Solubilized Inclusion Bodies 895 ml of refolding buffer (comprising 50 mM tris, 5% sorbitol, and total made up to 1000 ml milli Q water) was taken in the refolding vessel. 0.625 gm of cystine dihydrochloride solution was added to it. The pH of this solution was adjusted to 10.0 using 2M NaOH and the total volume was made up to 900 ml. The inclusion bodies solution was diluted at the rate of 5 ml/min over the period of 20 minutes with cysteine.

Ultrafiltration and pH Adjustment of the Refolded Protein

After the refolding of rHu GCSF, protein was concentrated by ultra-filtration. The pH of the concentrated protein sample was then adjusted to pH 4.00. The protein sample was then centrifuged at 8000 rpm (4° C.) for 30 minutes and the supernatant used as an input for aqueous two phase extraction step.

Multimodal Chromatographic Purification of Resolubilized Precipitate

The multimodal chromatography purification was carried out by using the below mentioned components.

Column: HEA Hypercel Prepacked 1.00 ml columns or PPA Hypercel Prepacked 1.00 ml columns Equilibration buffer: 50 mM acetate at pH 5.50 and 300 mM NaCl Elution buffer I: 50 mM acetate at pH 4.3 and 100 mm NaCl Elution buffer II: 100 mM citrate at pH 3.00

Load volume: 10.00 ml

Multimodal chromatography was performed using an ÄKTA Purifier chromatography system (GE Healthcare BioSciences, Uppsala, Sweden). Chromatography experiments involving HEA or PPA Hypercel resins were performed using prepacked 1 ml column (5 mm ID×50 mm from Pall Life sciences USA). Chromatography column was equilibrated using the selected equilibration buffer (5-10 CV). Pretreated GCSF protein solution was then injected into the chromatography column using a sample pump (GE Healthcare BioSciences). After sample loading unbound protein sample was removed using equilibration buffer wash step (5 CV). Elution step involves selective salt or pH based elution gradient. The output from the chromatography column was monitored using pH, conductivity and UV detection at 280, 260 and 215 nm. FIG. 2 shows the chromatogram for the multimodal chromatography for purification of rHu GCSF.

We preformed the multimodal chromatography with few other equilibration buffers and elution buffers I. The process for carrying out the procedure of multimodal chromatography remained the same as described above, with changes in the equilibration buffer and elution buffer 1.

The different equilibration buffers used for multimodal chromatography are mentioned below:
50 mM acetate at pH 5.70
50 mM acetate at pH 5.70 and 300 mM NaCl
50 mM acetate at pH 5.50 and 150 mM NaCl
50 mM acetate at pH 5.50 and 300 mm NaCl The different elution buffer 1 used for multimodal chromatography are mentioned below:
35 mM acetate at pH 4.3
50 mM acetate at pH 4.00 and 100 mM NaCl
50 mM acetate at pH 4.7 and 100 mM NaCl Biophysical Characterization of rHu GCSF Produced Using Multimodal Chromatography The biophysical characterization of rHu GCSF was done using various analytical tools and in-vitro bioassay as described in Example 1.

Example 4

Details of Analytical Tests

Various analytical tests were carried out for characterizing and quantifying the protein (rHu GCSF). The description of different analytical tests is provided below.

Absorbance Measurement at A280

Total protein in refold and chromatography outputs was determined using UV absorbance measurement at 280 nm. All filtrate fractions collected in Costar UV readable microtiter plates (Coming Incorporated, NY) were read at 280 nm using micro plate spectrophotometer sold under the trademark EPOCH™ (BioTek Instruments Inc. Winooski, Vt., USA). Pathlength correction factor was applied while measuring the A280.

Bradford's Assay for Total Protein Estimation

An orthogonal technique used for the total protein estimation was the Bradford's assay at 595 nm using micro plate spectrophotometer sold under the trademark EPOCH™ (BioTek Instruments Inc. Winooski, Vt., USA). After adding 5 μl of the sample into 250 μl of Bradford reagent, mixing was performed on the shaker for 30 seconds. After mixing, the sample was incubated in presence of the dye for 25 minutes and absorbance was measured at 595 nm. BSA was used as a standard protein for calibration curve preparation.

Reverse Phase HPLC Analysis for rHu GCSF Quantitation

Concentration of rHu GCSF in various chromatography outputs was determined using RP HPLC using a 4.6 mm×150 mm Zorbax Eclipse XDB C18 column (Agilent Technologies, Palo Alto, Calif.) on a Dionex Ultimate 3000 LC system. The mobile phase consisted of 0.1% (v/v) Trifluoroacetic acid (TFA) in water (solvent A) and 0.1% (v/v) TFA in 98% of acetonitrile (solvent B). Flow rate was maintained at 1 ml/min using a linear gradient of solvent A to solvent B at a wavelength of 214 nm. FIG. 4 shows the results of reverse phase HPLC used for checking the purity of rHu GCSF purified using the process described in the present invention. RP HPLC chromatogram was used to quantify the amount of oxidized and reduced impurities associated with the recombinant GCSF. Peak prior to the native GCSF peak corresponds to the oxidized form of the native GCSF whereas peak preceding the native main peak corresponds to the reduced form of native GCSF.

Size Exclusion Chromatography

Dimers and aggregates associated with rHu GCSF were analyzed by analytical size exclusion chromatography using the TSKgelG3000SWXL 7.8 mm×3000 mm and 5 μm particle size columns (Tosoh Bioscience, Stuttgart, Germany) and were detected by UV diode array detection at 215 nm. FIG. 5 shows the size exclusion chromatogram for rHu GCSF purified using the process described in the present invention. SEC chromatogram was used to quantify the amount of high molecular weight impurities associated with the recombinant GCSF. Peak prior to the native GCSF peak corresponds to dimer form of native GCSF.

SDS PAGE Analysis

SDS PAGE analysis was used for the identification of the impurities associated with rHu GCSF. A 1 mm thick resolving polyacrylamide gel (13%) was used under non reducing conditions at constant voltage conditions (150 V). Each sample was boiled for 5 min in the starting buffer before being loaded into the gel. Silver staining was used to detect proteins after electrophoretic separation. FIG. 6 shows the SDS PAGE analysis for studying the purity profile for the rHu GCSF purified using the process described in the present invention.

ELISA Analysis for Quantitation of Host Cell Proteins (HCP)

The host cell protein concentration in the process intermediate samples was analyzed using a two-site immune-enzymetric assay (*E. coli* HCP analysis kit F 410 from Cygnus Technologies, USA). Samples containing *E. coli* HCPs were reacted with horseradish peroxidase (HRP) enzyme labelled anti-*E. coli* antibody simultaneously in microtiter strips coated with an affinity purified capture anti-*E. coli* antibody. The immunological reactions resulted in the formation of a sandwich complex of solid phase antibody-HCP-enzyme labelled antibody. The microtiter strips are washed to remove any unbound reactants. The substrate, tetramethylbenzidine (TMB) was then reacted. The amount of hydrolyzed substrate was read on a microtiter plate reader at 450 nm and was directly proportional to the concentration of *E. coli* HCPs present. The output concentration of the HCP in the multimodal chromatography output is less than 100 PPM.

DNA Estimation

DNA from the process output samples was estimated using fluorescence assays sold under the trademark QUANT IT™ and PICOGREEN® (Invitrogen). The fluorescence assays sold under the trademark QUANT IT™ use advanced fluorophores that become fluorescent upon binding to DNA and the fluorescence intensity of the resulting complex depends directly on the amount of the DNA molecule in the sample. DNA estimation was performed using micro plate assay. Standard curve was prepared using double stranded lambda DNA. 20 µl of the process output sample way added to the 200 µl of diluted assay reagent sold under the trademark QUANT IT™ dsDNA BR Assay and the reaction mixture was incubated for 5 minutes. After five minutes fluorescence was measured using fluorescence spectrophotometer (excitation wavelength 480 nm and emission wavelength 520 nm). The output concentration of the double stranded DNA in the ATPS output is less than 10 ng.

We claim:

1. A method of purifying recombinant human granulocyte colony stimulating factor (rHu GCSF) from a recombinant host cell, wherein the method comprises:
   a) solubilizing inclusion bodies using a solubilization buffer to obtain solubilized rHu GCSF;
   b) refolding the solubilized rHu GCSF using a refolding buffer to obtain refolded rHu GCSF;
   c) concentrating the refolded rHu GCSF by ultra-filtration to obtain concentrated rHu GCSF;
   d) subjecting the concentrated rHu GCSF to aqueous two phase extraction to remove host cell proteins and host cell DNA and to obtain rHu GCSF partitioned into top phase and in the form of precipitate between the two aqueous phases;
   e) resolubilizing the rHu GCSF using a resulobilization buffer to obtain rHu GCSF solution; and
   f) subjecting the rHu GCSF solution to multimodal chromatography to obtain purified rHu GCSF, wherein the multimodal chromatography comprises:
      i) binding the rHu GCSF to multimodal chromatography resin with a buffer comprising 35 mM to 50 mM acetate and 0 mM to 450 mM sodium chloride with pH in the range of 5.10 to 5.70; and
      ii) eluting the rHu GCSF using an elution buffer comprising 10 mM to 50 mM acetate at pH ranging from 3.00 to 4.30 and 0 mM to 100 mM sodium chloride to obtain purified rHu GCSF, wherein the purified rHu GCSF has less than 1% methionine oxidized form of rHu GCSF, less than 0.5% reduced form of rHu GCSF, and less than 0.2% aggregated form of rHu GCSF.

2. A method of purifying recombinant human granulocyte colony stimulating factor (rHu GCSF) from a recombinant host cell, wherein the method comprises:
   a) solubilizing inclusion bodies using a solubilization buffer to obtain solubilized rHu GCSF;
   b) refolding the solubilized rHu GCSF using a refolding buffer to obtain refolded rHu GCSF;
   c) concentrating the refolded rHu GCSF by ultra-filtration to obtain concentrated rHu GCSF; and
   d) subjecting the concentrated rHu GCSF to multimodal chromatography to remove product related impurities, host cell proteins, and host cell nucleic acids and obtain purified rHu GCSF, wherein the multimodal chromatography comprises:
      i) binding the rHu GCSF to multimodal chromatography resin with a buffer comprising 35 mM to 50 mM acetate and 0 mM to 450 mM sodium chloride with the buffer pH lying in the range of 5.10 to 5.70; and
      ii) eluting the rHu GCSF using an elution buffer comprising 10 mM to 50 mM acetate at pH ranging from 3.00 to 4.30 and 0 mM to 100 mM sodium chloride to obtain purified rHu GCSF, wherein the purified rHu GCSF has less than 1% methionine oxidized form of rHu GCSF, less than 0.5% reduced form of rHu GCSF, and less than 0.2% aggregated form of rHu GCSF.

3. The method as claimed in claim 1, wherein the solubilization buffer comprises a combination of chaotropic reagent and reducing agent.

4. The method as claimed in claim 1, wherein the aqueous two phase extraction is carried out by mixing polymer and salt to the concentrated rHu GCSF, wherein the polymer concentration is in the range of 7.5% to 15.5% (w/w) and the salt concentration is in the range of 7.5% to 15.5% (w/w).

5. The method as claimed in claim 4, wherein the polymer is either ethylene oxide-propylene oxide copolymer or polyethylene glycol.

6. The method as claimed in claim 4, wherein the salt is selected from the group consisting of sodium phosphate, potassium phosphate, sodium sulphate, calcium sulphate, ammonium sulphate, ammonium phosphate, manganese sulphate, manganese phosphate, and calcium phosphate.

7. The method as claimed in claim 1, wherein the multimodal chromatography resin is selected from the group consisting of HEA Hypercel, Capto MMC, PPA Hypercel, Capto Adhere, MEP Hypercel, and Ceramic Hydroxyapatite.

8. The method as claimed in claim 1, wherein the binding of rHu GCSF to multimodal chromatography resin is carried out a pH less than pKa of the multimodal chromatography resin ligand.

9. The method as claimed in claim 2, wherein the multimodal chromatography resin is selected from the group consisting of HEA Hypercel, Capto MMC, PPA Hypercel, Capto Adhere, MEP Hypercel, and Ceramic Hydroxyapatite.

10. The method as claimed in claim 2, wherein the binding of rHu GCSF to multimodal chromatography resin is carried out a pH less than pKa of the multimodal chromatography resin ligand.

\* \* \* \* \*